US005750646A

United States Patent [19]
Coy et al.

[11] Patent Number: 5,750,646
[45] Date of Patent: *May 12, 1998

[54] BRADYKININ ANALOGS WITH NON-PEPTIDE BOND

[75] Inventors: David H. Coy, New Orleans, La.; Jacques-Pierre Moreau; John E. Taylor, both of Upton, Mass.; Sun Hyuk Kim, Chestnut Hill, Mass.

[73] Assignees: The Administrators of the Tulane Educational Fund, New Orleans, La.; Biomeasure, Inc., Hopkinton, Mass.

[*] Notice: The term of this patent shall not extend beyond the expiration date of Pat. No. 5,162,497.

[21] Appl. No.: 408,197

[22] Filed: Mar. 22, 1995

Related U.S. Application Data

[63] Continuation-in-part of Ser. No. 880,179, May 7, 1992, abandoned, which is a continuation-in-part of Ser. No. 282,328, Dec. 9, 1988, Pat. No. 5,162,497, which is a continuation-in-part of Ser. No. 257,998, Oct. 14, 1988, abandoned, which is a continuation-in-part of Ser. No. 248,771, Sep. 23, 1988, abandoned, which is a continuation-in-part of Ser. No. 207,759, Jun. 16, 1988, abandoned, which is a continuation-in-part of Ser. No. 204,171, Jun. 8, 1988, abandoned, which is a continuation-in-part of Ser. No. 173,311, Mar. 25, 1988, abandoned, which is a continuation-in-part of Ser. No. 100,571, Sep. 24, 1987.

[51] Int. Cl.⁶ .......................... A61K 38/00; C07K 5/00; C07K 7/00; C07K 17/00
[52] U.S. Cl. .......................... 530/314; 530/328; 530/332
[58] Field of Search .......................... 530/314, 328, 530/332; 514/15, 2, 803

[56] References Cited

U.S. PATENT DOCUMENTS

| | | | |
|---|---|---|---|
| 4,650,661 | 3/1987 | Szelke et al. | 424/9 |
| 4,693,993 | 9/1987 | Stewart et al. | 530/314 |
| 4,801,613 | 1/1989 | Stewart et al. | 530/314 |
| 4,803,261 | 2/1989 | Coy et al. | 530/333 |

FOREIGN PATENT DOCUMENTS

PCT/US91/2772 4/1991 WIPO.

OTHER PUBLICATIONS

Stewart, Handbook of EXPT'l. Pharmacology, (1979), pp. 227–272.
Martinez et al. J. Med. Chem., vol. 28, pp. 1874–1879, (1985).
Nagain et al. Peptides, vol. 8, pp. 1023–1028, (1987).
Rodriguez et al. J. Med. Chem., vol. 30 pp. 1366–1373, (1987).
Sasaki et al. J. Med. Chem., vol. 30, pp. 1162–1166, (1987).
Dubmevil et al. Drug Design and Delivery, vol. 2, pp. 49–54, (1987).

*Primary Examiner*—Avis M. Davenport
*Attorney, Agent, or Firm*—Fish & Richardson P.C.

[57] ABSTRACT

A linear peptide which is an analog of a naturally occurring, biologically active peptide having an active site and a binding site responsible for the binding of the peptide to a receptor on a target cell, cleavage of a peptide bond in the active site to the naturally occurring peptide being unnecessary for in vivo biological activity, the analog having a non-peptide bond instead of a peptide bond between an amino acid of the active site and an adjacent amino acid, and having the same binding site as the naturally occurring peptide, so that the analog is capable of acting as a competitive inhibitor of the naturally occurring peptide by binding to the receptor and, by virtue of the non-peptide bond, failing to exhibit the in vivo activity of the naturally occurring peptide.

3 Claims, No Drawings

BRADYKININ ANALOGS WITH NON-PEPTIDE BOND

This application is a continuation-in-part of U.S. patent application Ser. No. 07/880,179, filed May 7, 1992 now abandoned, which in turn is a continuation-in-part of U.S. patent application Ser. No. 282,328, filed Dec. 9, 1988, now U.S. Pat. No. 5,162,497, Nov. 10, 1992 which in turn is a continuation-in-part of U.S. patent application Ser. No. 257,998, filed Oct. 14, 1988, abandoned which in turn is a continuation-in-part of U.S. patent application Ser. No. 248,771, filed Sep. 23, 1988, abandoned which in turn is a continuation-in-part of Coy et al., U.S. patent application Ser. No. 207,759, filed Jun. 16, 1988, abandoned which in turn is a continuation-in-part of Coy et al., U.S. patent application Ser. No. 204,171, filed Jun. 8, 1988, abandoned which in, turn is a continuation-in-part of Coy et al., U.S. patent application Ser. No. 173,311, filed Mar. 25, 1988, abandoned which in turn is a continuation-in-part of Coy et al. U.S. patent application Ser. No. 100,571, filed Sep. 24, 1987, abandoned.

BACKGROUND OF THE INVENTION

This invention relates to therapeutic peptides useful, e.g., in cancer therapy or inflammation.

The amphibian peptide bombesin, pGlu-Gln-Arg-Leu-Gly-Asn-Gln-Trp-Ala-Val-Gly-His-Leu-Met-NH$_2$ (Anastasi et al., Experientia 27:166–167 (1971)), is closely related to the mammalian gastrin-releasing peptides (GRP), e.g., the porcine GRP. H$_2$N-Ala-Pro-Val-Ser-Val-Gly-Gly-Gly-Thr-Val-Leu-Ala-Lys-Met-Tyr-Pro-Arg-Gly-Asn-His-Trp-Ala-Val-Gly-His-Leu-met-(NH$_2$) (McDonald et al., Biochem. Biophys. Res. Commun. 90:227–233 (1979)) and human GRP. H$_2$N-Val-Pro-Leu-Pro-Ala-Gly-Gly-Gly-Thr-Val-Leu-Thr-Lys-Me t-Tyr-Pro-Arg-Gly-Asn-His-Trp-Ala-Val-Gly-His-Leu-Met-(NH$_2$). Bombesin has been found to be an autocrine or paracrine mitotic factor for a number of human cancer cell lines, including small-cell lung carcinoma (SCLC) (Haveman et al., eds. *Recent Results in Cancer Research—Peptide Hormones in Lung Cancer*, Springer-Verlag, New York:1986). A number of these cancers are known to secrete peptide hormones related to GRP or bombesin. Consequently, antagonists to bombesin have been proposed as agents for the treatment of these cancers.

Cuttitta et al. demonstrated that a specific monoclonal antibody to bombesin inhibited in vivo the growth of a human small-cell lung cancer cell line xenografted to nude mice (Cuttitta et al., Cancer Survey 4:707–727 (1985)). In 3T3 murine fibroblasts which are responsive to the mitotic effect of bombesin, Zachary and Rozengurt observed that a substance P antagonist (Spantide) acted as a bombesin antagonist (Zachary et al., Proc. Natl. Acad. Sci. (USA), 82:7616–7620 (1985)). Heinz-Erian et al. replaced His at position 12 in bombesin with D-Phe and observed bombesin antagonist activity in dispersed acini from guinea pig pancreas (Heinz-Erian et al., Am. J. of Physiol. 252:G439–G442 (1987)). Rivier reported on work directed toward restricting the conformational freedom of the bioactive C-terminal decapeptide of bombesin by incorporating intramolecular disulfide bridges; however, Rivier mentioned that, so far, bombesin analogs with this modification fail to exhibit any antagonist activity (Rivier et al., "Competitive Antagonists of Peptide Hormones," in Abstracts of the International Symposium on Bombesin-Like Peptides in Health and Disease, Rome (October, 1987). Abbreviations (uncommon):

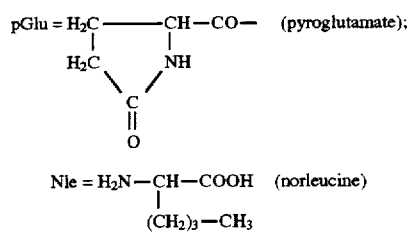

Nle = H$_2$N—CH—COOH (norleucine)
|
(CH$_2$)$_3$—CH$_3$

Pal=3-pyridyl-alanine
Nal=naphthylalanine
Sar=sarcosine

SUMMARY OF THE INVENTION

In general, the invention features a linear (i.e., non-cyclic) peptide which is an analog of a naturally occurring, biologically active peptide having an active site and a binding site responsible for the binding of the peptide to a receptor on a target cell, cleavage of a peptide bond in the active site of the naturally occurring peptide being unnecessary for in vivo biological activity, the analog having a non-peptide bond instead of a peptide bond between an amino acid of the active site and an adjacent amino acid, the analog being capable of binding to the receptor, so that the analog is capable of acting as a competitive inhibitor of the naturally occurring peptide by binding to the receptor and, by virtue of the non-peptide bond, failing to exhibit the in vivo activity of the naturally occurring peptide. (A detailed discussion of the chemistry of non-peptide bonds is given in Coy et al. (1988) Tetrahedron 44,3:835–841, hereby incorporated by reference.) Preferably, the naturally occurring peptide is characterized in that one or more amino acids in the amino terminal half of he peptide are hydrogen bonded to one or more amino acids in the carboxy terminal half of the peptide, and the non-peptide bond of the linear peptide decreases that hydrogen bonding, thereby destroying biological activity. It is believed that many of the linear peptides of the invention are analogs of peptides whose biological activity depends at least in part on their ability to form tertiary "hairpin" configurations in which amino acids in the amino terminal ("left") half of the molecule are hydrogen bonded to amino acids in the carboxy terminal ("right") half of the molecule, and that the pseudopeptide bond or statine or AHPPA residue introduced according to the invention interferes with this hydrogen bonding, hindering the formation of the hairpin configuration on which activity depends. One may expect the loss of the ability to hydrogen bond to affect the biological activity of the molecule either by the loss of structural stability conferred by the transannular bonding or by the inability of the backbone to hydrogen bond to the receptor. Additionally, the increased flexibility of the molecule about the reduced bond compared with the rigidity of the normal peptide amide bond is expected to alter the conformational integrity of the molecule and thus its biological activity.

It is apparent from the above that the linear peptides for which introduction of a pseudopeptide bond is useful in creating or enhancing antagonist activity are those in which activity is associated with a site within the amino acid chain (some peptides, e.g., CCK, Have their active sites at an end of the peptide). The pseudopeptide bond can be introduced in a region involved in receptor binding, or in a non-binding region; it has been shown (Nagain et al., Peptides, 8:1023–28 (1987)) that a pseudopeptide bond introduced in the binding region does not prevent binding. Generally, useful classes of peptides in which this modification can be made are those in which at least one amino acid involved in the active site is located in the carboxy terminal half of the molecule; the non-peptide bond is introduced between this amino acid and one adjacent to it.

One class of peptides of the invention is an effective mammalian GRP or amphibian bombesin antagonist peptide of formula (1):

$$R_1\diagdown$$
$$\phantom{R_1}A^1-A^2-A^3-A^4-A^5-A^6-A^7-Trp-A^9-A^{10}$$
$$R_2\diagup$$

$$\phantom{xxxxxxxxxxxxxx}\diagup R_3$$
$$A^{11}-A^{12}-A^{13}-A^{14}-N$$
$$\phantom{xxxxxxxxxxxxxxxx}\diagdown R_4$$

wherein $A^1$=pGlu, D or L, or is deleted;

$A^2$=Gln, Asn, Gly, Ala, Leu, Ile, Nle, α-aminobutyric acid, Met, Val, Phe, p-X-Phe (X=F, Cl, Br, OH or $CH_3$), Trp, β-naphthylalanine or is deleted;

$A^3$=Arg, D-Arg, Lys, D-Lys or is deleted;

$A^4$=Gln, Asn, Gly, Ala, Leu, Ile, Nle, α-aminobutyric acid, Met, Val, Phe, p-X-Phe (X=F, Cl, Br, OH or $CH_3$), Trp, β-naphthylalanine or is deleted;

$A^5$=Gln, Asn, Gly, Ala, Leu, Ile, Nle, α-aminobutyric acid, Met, Val, Phe, p-X-Phe (X=F, Cl, Br, OH or $CH_3$), Trp, β-naphthylalanine, D or L, or is deleted;

$A^6$=Gln, Asn, Gly, Ala, N-Ac-D-Ala, Leu, Ile, Nle, α-aminobutyric acid, Met, Val, Phe, p-X-Phe (X=F, Cl, Br, OH or $CH_3$), Trp, p-Glu, Sar, β-naphthylalanine, D or L, or is deleted;

$A^7$=Gln, Asn, Gly, Ala, Leu, Ile, Nle, α-aminobutyric acid, Met, Val, Phe, D-Phe, p-X-Phe (X=F, Cl, Br, OH or $CH_3$), Trp, Lys, His, or β-naphthylalanine;

$A^8$=Trp, Met;

$A^9$=Gln, Asn, Gly, Ala, Leu, Ile, Nle, α-aminobutyric acid, Met, Val, Phe, p-X-Phe (X=F, Cl, Br, OH or $CH_3$), Trp, or β-naphthylalanine, D or L;

$A^{10}$=Gln, Asn, Gly, Ala, Leu, Ile, Nle, α-aminobutyric acid, Met, Val, Phe, p-X-Phe (X=F, Cl, Br, OH or $CH_3$), Trp, Thr, or β-naphthylalanine;

$A^{11}$=Gly, Ala, Phe, D or L;

$A^{12}$=His, Phe, or p-X-Phe (X=F, Cl, Br, OH, $CH_3$), D or L;

$A^{13}$=Gln, Asn, Gly, Ala, Leu, Ile, Nle, α-aminobutyric acid, Met, Val, Phe, p-X-Phe (X=F, Cl, Br, OH or $CH_3$), Trp, or β-naphthylalanine;

$A^{14}$=Gln, Asn, Gly, Ala, Leu, Ile, Nle, α-aminobutyric acid, Met, Val, Phe, p-X-Phe (X=F, Cl, Br, OH or $CH_3$), Trp, or β-naphthylalanine;

provided that each $R_1$, $R_2$, $R_3$ and $R_4$, independently, is H, $C_{1-12}$ alkyl, $C_{7-10}$ phenylalkyl, $COE_1$ (where $E_1$ is $C_{1-20}$ alkyl, $C_{3-20}$ alkenyl, $C_{3-20}$ alkinyl, phenyl, naphthyl, or $C_{7-10}$ phenylalkyl), or $COOE_2$ (where $E_2$ is $C_{1-10}$ alkyl or $C_{7-10}$ phenylalkyl), and $R_1$ and $R_2$ are bonded to the N-terminal amino acid of said peptide, which can be $A^1$, $A^2$, $A^3$, $A^4$, $A^5$, $A^6$, or $A^7$, provided that when one of $R_1$ or $R_2$ is $COE_1$ or $COOE_2$, the other must be H, and when one of $R_3$ or $R_4$ is $COE_1$ or $COOE_2$, the other must be H, and further provided that when $A^1$=pGlu, $R_1$ must be H and $R_2$ must be the portion of Glu that forms the imine ring in pGlu; and for each of the residues $A^7$, $A^8$, $A^9$, $A^{11}$, $A^{12}$, and $A^{13}$, independently, the carbon atom participating in the amide bond between that residue and the nitrogen atom of the alpha amino group of the adjacent amino acid residue may be a carbonyl carbon or may be reduced to a methylene carbon, provided that at least one such carbon atom must be reduced to a methylene carbon (i.e., at least one of the subject peptide CONH bonds must be replaced by a non-peptide, i.e., pseudopeptide, $CH_2NH$ bond); or a pharmaceutically acceptable salt thereof. (Where no D- or L-isomeric designation is given herein, the naturally occurring L-isomer is intended.)

Preferably, an bombesin antagonist peptide has, for each of the residues $A^{11}$, $A^{12}$, and $A^{13}$, independently, the carbon atom participating in the amide bond between that residue and the nitrogen atom of the alpha amino group of the adjacent amino acid residue which may be a carbonyl carbon or may be reduced to a methylene carbon, provided that at least one such carbon atom must be reduced to a methylene carbon; or a pharmaceutically acceptable salt thereof. Most preferably, the bombesin antagonist peptide has $A^1$ through $A^6$ deleted and the carbon atom participating in the amide bond between $Leu^{13}$ and $Leu^{14}$ is a methylene carbon, or a pharmaceutically acceptable salt thereof.

Two other classes of peptides of the invention are mammalian GRP or amphibian bombesin-related peptides derived from (1) litorin or (2) neuromedin and of the amino acid formula (1):

$$R_1\diagdown\phantom{xxxxxxxxxxxxxxxxxx}\diagup R_3$$
$$\phantom{R_1}A^1-A^2-A^3-A^4-A^5-A^6-A^7-A^8-A^9(-A^{10})$$
$$R_2\diagup\phantom{xxxxxxxxxxxxxxxxxx}\diagdown R_4$$

wherein for litorin derivatives $A^1$ through $A^9$ correspond to positions $A^6$ through $A^{14}$ of claim 6, or wherein for neuromedin derivatives $A^1$ through $A^{10}$ corresponds to positions $A^5$ through $A^{14}$ of claim 6; provided that, for both (1) and (2), the carbon atom participating in the amide bond between the $A^8$ residue of Litorin or the $A^9$ residue of neuromedin and the nitrogen atom of the alpha amino group of the adjacent amino acid residue may be a carbonyl carbon or may be reduced to a methylene carbon, or a pharmaceutically acceptable salt thereof.

Peptides of the invention that contain a pseudo-peptide bond substitution within the active site of the naturally occurring peptide are antagonists to the biological activity of the naturally occurring bombesin peptide, with one exception; the linear analog of bombesin BIM-26027. This analog has the amino acid formula pGlu-Gln-Arg-Leu-Gly-Asn-Gln-Trp-Ala-Valψ[$CH_2NH$]-Gly-His-Leu-$Leu^4$ and is an agonist of the biological activity of naturally occurring bombesin. (Non-peptide bonds are symbolized herein by "ψ[$CH_2NH$]" or "ψ".) Therefore, a third class of peptides of the invention are effective mammalian GRP or amphibian bombesin agonists of the formula (1) recited above, including, for the residue $A^{10}$, the carbon atom participating in the amide bond between the residue and the nitrogen atom of the alpha amino group of the adjacent amino acid residue may be a carbonyl carbon or may be a nonpeptide bond, provided that the nonpeptide bond may be a carbonyl carbon having been reduced to a methylene carbon, further provided that at least one such carbon atom must be reduced to a methylene carbon; or a pharmaceutically acceptable salt thereof. Most preferred is the bombesin agonist BIM-26027 having the amino acid formula pGlu-Gln-Arg-Leu-Gly-Asn-Gln-Trp-Ala-Valψ[CH$_2$NH]-Gly-His-Leu-Leu$^{14}$.

Other agonist analogues are peptides in which the pseudopeptide bond is not located within the active site, or in which two amino acid residues of the active site are replaced by statine or AHPPA. (Statine has the chemical structure $$\begin{array}{c} CH_3 \diagdown \diagup CH_3 \\ CH \\ | \\ CH_2 \ \ OH \\ | \ \ \ \ \ | \\ NH_2-CH-CH-CH_2-CO_2H \end{array}$$

and statine-amide has the structure $$\begin{array}{c} CH_3 \diagdown \diagup CH_3 \\ CH \\ | \\ CH_2 \ \ OH \\ | \ \ \ \ \ | \\ NH_2-CH-CH-CH_2-CONH_2 \end{array}$$

and AHPPA has the formula:

((3S,4S)-4-amino-3-hydroxy-5-phenylpentanoic acid.)

Therefore, a fourth class of peptides of the invention is that effective as an agonist in which the active site includes the positions A$^9$, A$^{10}$, A$^{11}$, A$^{12}$, and A$^{13}$, the active site having either (a) a nonpeptide bond outside of the active site of bombesin, or (b) having at least one statine or AHPPA residue in place of two naturally occurring amino acids of the active site; the active site can contain statine or AHPPA when all bonds between amino acid residues are peptide bonds; when an amino acid residue is statine or AHPPA, the amino acid to the right of it in the formula is deleted, so that the analog is capable of binding to a receptor and, by virtue of said statine or AHPPA residue, exhibits enhanced in vivo biological activity compared to the naturally occurring peptide. The most preferred peptide of this class is the bombesin agonist BIM-26096 having the amino acid formula pGlu-Gln-Arg-Leu-Gly-Asn-Gln-Trp-Ala-Val-Gly-His-[Sta$^{13}$,Des Met$^{14}$-NH$_2$.

The bombesin, neuromedin and litorin antagonists and agonists of the invention are suitable for the treatment of all forms of cancer where bombesin-related substances act as autocrine or paracrine mitotic factors, especially pancreas and small-cell lung carcinoma. In addition, any of these analogs tagged with a radioactive label can be used for imaging tumors that express the bombesin receptor, e.g., small cell lung tumors.

In formula (1), when R$_1$, R$_2$, R$_3$ or R$_4$ is an aromatic, lipophilic group, the in vivo activity can be long lasting, and delivery of the compounds of the invention to the target tissue (e.g., the lungs) can be facilitated.

Another class of peptides of the invention is bradykinin ("BK") analogs effective in vasoconstriction or vasodilation and of the amino acid formula (2):

Q-A$^1$-A$^2$-A$^3$-Gly-A$^5$-A$^6$-A$^7$-A$^8$-A$^9$-Z$^{10}$ wherein

Q=L-Arg, D-Arg, L-homo-Arg, D-homo-Arg, L-Lys, D-Lys, lower (1–5 carbon atoms) Σ-N-alkyl-L-Lys, lower Σ-N-alkyl-D-Lys, lower Σ-N-alkyl-L-His, lower Σ-N-alkyl-D-His, lower Σ-N-alkyl-L-Pal, lower Σ-N-alkyl-D-Pal, acetyl, lower acyl, or lower α-N-alkyl;

A$^1$ and A$^9$ (independently)=L- or D-Arg, L- or D-homo-Arg, L- or D-Lys, lower Σ-N-alkyl-Lys, His, or Pal;

A$^2$=Pro, hydroxy-Pro("Hyp"), or N-Me-Ala

A$^3$=Pro, hydroxy-Pro, or N-Me-Ala;

A$^5$ and A$^8$ (independently)=Phe, thienylalanine, His, Trp, Nal, Pal, or P-X-Phe (X=F, Cl, Br, OH, or CH$_3$);

A$^6$=Ser, Thr, Ala, Leu, Ile, Val, or Tyr;

A$^7$=Pro, hydroxy-Pro, N-Me-Ala, D-Phe, or D-thienylalanine;

Z$^{10}$=OH, COOH, NH$_2$, or lower alkylamide;

provided that, for each of the residues A$^5$, A$^6$, A$^7$, and A$^8$, independently, the carbon atom participating in the amide bond between that residue and the nitrogen atom of the alpha amino group of the adjacent amino acid residue may be a carbonyl carbon or may be reduced to a methylene carbon, provided that at least one such carbon atom must be reduced to a methylene carbon (i.e., at least one of the subject peptide CONH bonds must be replaced by a non-peptide CH$_2$NH bond); or a pharmaceutically acceptable salt thereof.

A preferred bradykinin antagonist of the invention is H-Arg-Pro-Pro-Gly-Phe-Ser-Pro-Phe-ψ[CH$_2$NH]Arg-OH.

The bradykinin peptides of the invention are useful for preventing increased vascular tone and noninfectious inflammation, as analgesics, for preventing edema due to pulmonary brain trauma, in preventing shock due to hemorrhage, or for any condition characterized by vasodilation-induced swelling and/or itching. Bradykinin agonists may be useful in the repair of tissue damage. The bradykinin peptides of the invention may act as antagonists by the mechanism described above for all peptides, or may appear antagonistic due to a different mechanism, such as over-stimulation of the bradykinin receptor to the point where the receptor is no longer responsive.

Other features and advantages of the invention will be apparent from the following description of the preferred embodiments thereof, and from the claims.

DESCRIPTION OF THE PREFERRED EMBODIMENTS

We will first briefly describe the tables.

Tables

Table I shows formulas for the bombesin pseudo-peptide analogues and results of in vitro inhibition of [$^{125}$I]GRP binding to cerebral cortex, 3T3 fibroblast or murine fibroblast bombesin receptors, and bombesin-stimulated ($^3$H) Thymidine uptake by cultured 3T3 cells.

Table II shows formulas for LHRH antagonists of the invention.

Table III shows formulas for bradykinin pseudo-peptide analogues and results of in vitro inhibition of receptor binding and cyclic GMP formation.

We now describe the structure, synthesis, and use of the preferred embodiments of the invention.

Structure

The peptides of the invention all have a non-peptide bond in at least one of the indicated position, except for the statine or AHPPA substituted analogs, such as sta$^{13}$-des Met$^{14}$ bombesin. By non-peptide bond is meant that the carbon atom participating in the bond between two residues is reduced from a carbonyl carbon to a methylene carbon. The peptide bond reduction method which yields this non-peptide bond is described in Coy et al., U.S. patent application, Ser. No. 879,348, now U.S. Pat. No. 4,803,261, issued Feb. 7, 1989, assigned to the same assignee as the present application, hereby incorporated by reference. Any one or all of the amino acids in positions 1 through 6 of the bombesin antagonists may be deleted from the peptides, and the peptides are still active as antagonists.

The peptides of the invention can be provided in the form of pharmaceutically acceptable salts. Examples of preferred salts are those with therapeutically acceptable organic acids, e.g., acetic, lactic, maleic, citric, malic, ascorbic, succinic, benzoic, salicylic, methanesulfonic, toluenesulfonic, or pamoic acid, as well as polymeric acids such as tannic acid or carboxymethyl cellulose, and salts with inorganic acids such as the hydrohalic acids, e.g., hydrochloric acid, sulfuric acid, or phosphoric acid.

Synthesis of Bombesin Analogs

The synthesis of the bombesin antagonist pGlu-Gln-Arg-Leu-Gly-Asn-Gln-Trp-Ala-Val-Gly-His-Leuψ[$CH_2$—NH]Leu-$NH_2$ follows. Other bombesin antagonists and agonists and antagonists of other peptides can be prepared by making appropriate modifications of the following synthetic method.

The first step is the preparation of the intermediate pGlu-Gln-Arg(tosyl)-Leu-Gly-Asn-Gln-Trp-Ala-Val-Gly-His(benzyloxycarbonyl)-Leuψ[$CH_2NH$] Leu-benzhydrylamine resin, as follows.

Benzhydrylamine-polystyrene resin (Vega Biochemicals, Inc.) (0.97 g, 0.5 mmole) in the chloride ion form is placed in the reaction vessel of a Beckman 990B peptide synthesizer programmed to perform the following reaction cycle: (a) methylene chloride; (b) 33% trifluoroacetic acid (TFA) in methylene chloride (2 times for 1 and 25 min. each); (c) methylene chloride; (d) ethanol; (e) methylene chloride; and (f) 10% triethylamine in chloroform.

The neutralized resin is stirred with alpha-t-butoxycarbonyl(Boc)-leucine and diisopropylcarbodiimide (1.5 mmole each) in methylene chloride for 1 hour, and the resulting amino acid resin is then cycled through steps (a) to (f) in the above wash program. Boc-leucine aldehyde (1.25 mmoles), prepared by the method of Fehrentz and Castro, Synthesis, p. 676 (1983), is dissolved in 5 ml of dry dimethylformamide (DMF) and added to the resin TFA salt suspension followed by the addition of 100 mg (2 mmoles) of sodium cyanoborohydride (Sasaki and Coy, Peptides 8:119–121 (1987); Coy et al., id.). After stirring for 1 hour, the resin mixture is found to be negative to ninhydrin reaction (1 min.), indicating complete derivatization of the free amino group.

The following amino acids (1.5 mmole) are then coupled successively in the presence diisopropylcarbodiimide (1.5 mmole), and the resulting amino acid resin is cycled through washing/deblocking steps (a) to (f) in the same procedure as above: Boc-His(benzyloxycarbonyl), Boc-Gly, Boc-Val, Boc-Ala, Boc-Trp, Boc-Gln (coupled in the presence of equivalent of hydroxybenzotriazole), Boc-Asn (coupled in the presence of 1 equivalent of hydroxybenzotriazole), Boc-Gly (coupled as a 6M excess of the p-nitrophenyl ester), Boc-Leu, Boc-Arg(tosyl), Boc-Gln (coupled as a 6 M excess of the p-nitrophenylester), and pGlu. The completed resin is then washed with methanol and air dried.

The resin described above (1.6 g, 0.5 mmole) is mixed with anisole (5 ml) and anhydrous hydrogen fluoride (35 ml) at 0° C. and stirred for 45 min. Excess hydrogen fluoride is evaporated rapidly under a stream of dry nitrogen, and free peptide is precipitated and washed with ether. The crude peptide is dissolved in a minimum volume of 2M acetic acid and eluted on a column (2.5×100 mm) of Sephadex G-25 (Pharmacia Fine Chemicals, Inc.). Fractions containing a major component by uv absorption and thin layer chromatography (TLC) are then pooled, evaporated to a small volume and applied to a column (2.5×50 cm) of octadecylsilane-silica (Whatman LRP-1, 15–20 μm mesh size).

The peptide is eluted with a linear gradient of 0–30% acetonitrile in 0.1% trifluoroacetic acid in water. Fractions are examined by TLC and analytical high performance liquid chromatography (HPLC) and pooled to give maximum purity. Repeated lyophilization of the solution from water gives 60 mg of the product as a white, fluffy powder.

The product is found to be homogeneous by HPLC and TLC. Amino acid analysis of an acid hydrolysate confirms the composition of the peptide. The presence of the Leuψ[$CH_2$—NH]Leu bond is demonstrated by fast atom bombardment mass spectrometry.

pGlu-Gln-Arg-Leu-Gly-Asn-Gln-Trp-Alaψ[$CH_2$—NH]Val-Gly-His-Leu-Met-$NH_2$ and pGlu-Gln-Arg-Leu-Gly-Asn-Gln-Trp-Ala-Val-Gly-His-Leuψ[$CH_2NH$]Met-$NH_2$ or other peptides are prepared in similar yields in an analogous fashion by appropriately modifying the above procedure.

A statine or AHPPA residue can be substituted in place of any two amino acids of the peptide, where the peptide contains no pseudopeptide bonds. For example, sta[13]-des Met[14] bombesin was prepared in an analagous fashion by first coupling statine to the resin and then proceeding with the addition of Boc-His(benzylocarbonyl). Statine or Boc-statine can be synthesized according to the method of Rich et al., 1978, J. Organic Chem. 43; 3624; and Rich et al., 1980, J. Med. Chem. 23:27, and AHPPA can be synthesized according to the method of Hui et al., 1987, J. Med. Chem. 30:1287.

Synthesis of Sta[13]-Des-Met[14] Bombesin

Solid-phase synthesis of the peptide pGlu-Gln-Arg-Leu-Gly-Asn-Gln-Trp-Ala-Val-Gly-His-Sta-$NH_2$ was accomplished through the use of the following procedures in which alpha-t-butoxycarbonyl statine (prepared by the procedure of Rich et al., J. Org. Chem. 1978, 43, 3624) is first coupled to methylbenzhydrylamine-polystyrene resin. After acetylation, the intermediate p-Glu-Gln-Arg(tosyl)-Leu-Gly-Asn-Gln-Trp-Ala-Val-Gly-His(benzyloxycarbonyl)-Sta-methylbenzhydrylamine resin is prepared. The synthetic procedure used for this preparation follows in detail:

1. Incorporation of alpha-t-butoxycarbonyl statine on methylbenzhydrylamine resin Methylbenzhydrylamine-polystyrene resin (Vega Biochemicals, Inc.) (1.0 g, 0.73 mmol) in the chloride ion form is placed in the reaction vessel of a Vega 250C Coupler peptide synthesizer. The synthesizer was programmed to perform the following reactions: (a) methylene chloride; (b) 10% triethylamine in chloroform; (c) methylene chloride; and (d) dimethylformamide.

The neutralized resin is mixed for 18 hours with the preformed active ester made from alpha-t-butoxycarbonyl statine (1.46 mmol), diisopropyl carbodiimide (2 mmol), and hydroxybenzotriazole hydrate (1.46 mmol in dimethylformamide at 0° C. for one hour. The resulting amino acid resin is washed on the synthesizer with dimethylformamide and then methylene chloride. The resin mixture at this point was found by the Kaiser ninhydrin test (5 minutes) to have an 84% level of statine incorporation on the resin.

Acetylation was performed by mixing the amino-acid resin for 15 minutes with N-acetyl imidazole (5 mmol) in methylene chloride. Derivatization to the 94–99% level of the free amino groups of the resin was indicated by the Kaiser ninhydrin test (5 minutes). The Boc-statine-resin is then washed with methylene chloride.

2. Couplings of the Remaining Amino Acids

The peptide synthesizer is programmed to perform the following reaction cycle: (a) methylene chloride; (b) 33% triflouroacetic acid (TFA) in methylene chloride (2 times for 5 and 25 min. each); (c) methylene chloride; (d) isopropyl alcohol; (e) 10% triethylamine in chloroform; and (f) methylene chloride.

The following amino acids (2.19 mmol) are then coupled successively by diisopropyl carbodiimide (4 mmol) alone or diisopropyl carbodiimide (4 mmol) plus hydroxybenzotriazole hydrate (1.47 or 0.73 mmol) and the resulting peptide-resin is washed on the synthesizer with dimethylformamide and then methylene chloride, and then cycled through the washing and deblocking steps (a) to (f) in the procedure described above.

Boc-His (benzyloxycarbonyl) (coupled in the presence of 2 equivalents hydroxybenzotriazole); Boc-Gly; Boc-Val; Boc-Ala; Boc-Trp; Boc-Gln and Boc Asn (coupled as the preformed hydroxybenzotriazole active esters made by reaction at 0° C. for one hour with 1 equivalent hydroxybenzotriazole hydrate); Boc-Gly; Boc-Leu; Boc-Arg(tosyl), Boc-Gln, and pGlu (also coupled as the preformed active esters of hydroxybenzotriazole made by reaction at 0° C. for one hour with 1 equivalent hydroxybenzotriazole hydrate). The completed peptide-resin is then washed with methanol and air dried.

The peptide-resin described above (1.60 g, 0.73 mmol) is mixed with anisole (2.5 mL), dithioerythreitol (50 mg), and anhydrous hydrogen fluoride (30 mL) at 0° C. for one hour. Excess hydrogen fluoride is evaporated rapidly under a stream of dry nitrogen, and the free peptide is precipitated and washed with ether. The crude peptide is dissolved in 100 mL of 1M acetic acid and the solution is then evaporated under reduced pressure. The crude peptide is dissolved in a minimum volume of methanol/water 1/1 and triturated with 10 volumes of ethyl acetate.

The triturated peptide is applied to a column (9.4 mm I.D.×50 cm) of octadecylsilane-silica (Whatman Partisil 10 ODS-2M 9). The peptide is eluted with a linear gradient of 20–80% of 20/80 0.1% trifluoroacetic acid/acetonitrile in 0.1% trifluoroacetic acid in water. Fractions are examined by TLC and analytical high performance liquid chromatography (HPLC) and pooled to give maximum purity. Lyophilization of the solution from water gives 77 mg of the product as a white fluffy powder.

Other compounds can be prepared as above and tested for effectiveness as agonists or antagonists in the following test program.

Phase 1—3T3 Peptide Stimulated [3H] Thymidine Uptake Assay

Cell Culture. Stock cultures of Swiss 3T3 cells (American Type Culture Collection No. CCL 92) are grown in Dulbecco's Modified Eagles Medium (DMEM) supplemented with 10% fetal calf serum in humidified atmosphere of 10% $CO_2$/90% air at 37° C. For experimental use, the cells are seeded into 24-well cluster trays and used four days after the last change of medium. The cells are arrested in the G1/G0 phase of the cell cycle by changing to serum-free DMEM 24 hours prior to the thymidine uptake assay.

Assay of DNA Synthesis. The cells are washed twice with 1 ml aliquots of DMEM (−serum) then incubated with DMEM (−serum), 0.5 µM [methyl-$^3$H] thymidine (20 Ci/mmole, New England Nuclear), bombesin (1 nM), and four concentrations of the test compounds (1, 10, 100, 1000 nM) in a final volume of 0.5 ml. After 28 hours at 37° C., [methyl-$^3$H] thymidine incorporation into acid-insoluble pools is assayed as follows. The cells are washed twice with ice-cold 0.9% NaCl (1 ml aliquots), and acid soluble radioactivity is removed by a 30 min. (4° C.) incubation with 5% trichloroacetic acid (TCA). The cultures are then washed once (1 ml) with 95% ethanol and solubilized by a 30 min. incubation (1 ml) with 0.1N NaOH. The solubilized material is transferred to vials containing 15 ml ScintA (Packard), and the radioactivity is determined by liquid scintillation spectrometry.

Phase 2—Small Cell Carcinoma (SCLC)—Bombesin Stimulated [$^3$H] Thymidine Uptake Assay Cell Culture. Cultures of the human cell carcinoma cell line (NCI-H69) (obtained from the American Type Culture Association) are maintained in RPMI 1640 medium supplemented with 10% fetal calf serum in 10% $CO_2$/90% air at 37° C. Twenty-four hours prior to assay, the cells are washed with serum-free medium and seeded in 24-well cluster trays.

Assay of DNA Synthesis. Bombesin (1 nM), 0.5 µM [methyl-$^3$H] thymidine (20 Ci/mmole, New England Nuclear), and four concentrations of the test compounds (1, 10, 100, 1000 nM) are added to the cultures to achieve a final volume of 0.5 ml. After a 28 hr incubation at 37° C., the cells are collected onto GF/B glass fiber filters, and the DNA is precipitated with ice-cold TCA. [$^3$H] thymidine incorporation into acid-insoluble fractions of DNA is determined by liquid scintillation spectrometry.

Phase 3—Peptide-Induced Pancreatitis

Male, Sprague-Dawley rats (250 g) are used for these experiments. The test compound, or 0.9% NaCl is administered s.c. 15 min. prior to the bombesin injection. Bombesin injections are given s.c. at a dose of 10 µg/kg, and blood samples are obtained at 1 hr. 30 min., 3 hr. and 6 hr. Plasma amylase concentration are determined by the Pantrak Amylase test.

Phase 4—In-Vitro Inhibition of [$^{125}$I] Gastrin Releasing Peptide (GRP) Binding to Bombesin Receptors Membranes from various tissues (rat brain, rat pancreas, rat anterior pituitary, SCLC, 3T3 cells) are prepared by homogenization in 50 mM TrisHCl containing 0.1% bovine serum albumin and 0.1 mg/ml bacitracin followed by two centrifugations (39,000×g×15 min., 4° C.) with an intermediate resuspension in fresh buffer. For assay, aliquots (0.8 ml) are incubated with 0.5 nM [$^{125}$I]GRP (2000 Ci/mmol, Amersham Corp.) and various concentrations of the test compounds in a final volume of 0.5 ml. After a 30 minute incubation at 4° C., the binding reaction is terminated by rapid filtration through Whatman GF/C filters that have been pre-soaked in 0.3% aqueous polyethyleneimine to reduce the level of nonspecific binding. The filters and tubes are washed three times with 4 ml aliquots of ice-cold buffer, and the radioactivity trapped on the filters is counted by gamma-spectrometry. Specific binding is defined as the total [$^{125}$I] GRP bound minus that bound in the presence of 1000 nM bombesin.

Phase 5—Inhibition of Gastrin Release

The stomachs of anesthetized rats are perfused with saline collected over 15 minute periods via pyloric cannulation while the test peptide is infused through the femoral vein for periods between 0 and 150 minutes.

Results of Assays of Test Peptides

A number of analogs of bombesin, each containing a non-peptide bond, were synthesized and tested in one or more of the above-described Phase 1–5 assays; the results of Phase 1, 2 and 4 tests are given in Table 1 attached hereto (analogs of bombesin are indicated by the symbol "BN").

Brain and 3T3 GRP receptor and thymidine uptake data are expressed in IC50 (nM). Table 1 also gives results for non-peptide bond-containing analogs of three other naturally-occurring peptides, Substance P (which plays a role in the sensation of pain), Neuromedin C, whose C-terminal seven amino acids are similar to those of bombesin, and litorin, whose eight C-terminal amino acids are identical to Bombesin, with the exception of a Phe substitution for Leu at position $A^{13}$ of bombesin.

In the Tables or text, she position of the non-peptide bond is indicated by the position of the symbol $\psi$; i.e., $\psi$ is always shown following the amino acid which, in that peptide, is bonded to the next sequential (i.e., toward the C-terminus) amino acid via the non-peptide bond.

In Table 1, it can be seen that a preferred placement of the non-peptide bond in bombesin analogs is at the 13-14 position; two of the most active analogs (as indicated by a low GRP receptor IC50 value) are BIM-26027 and BIM-26028. However, BIM-26027 causes proliferation of cancer cells (see Table 1, under thymidine uptake), and therefore is an agonist and not an antagonist. In general, compounds having the non-peptide bond at any position other than the active site of the peptide are agonists rather than antagonists. Table I also shows that when statine replaces the $A^{13}$ and $A^{14}$ residues of bombesin, the resultant analog BIM-26096 causes proliferation of cancer cells and is therefore an agonist. Bombesin superagonists may be useful in cancer therapy, as suggested by Alexander et al., 1988, Pancreas 3:297, and Alexander et al., 1988, Cancer Research 48:1439–1441, hereby incorporated by reference. Alexander et al. showed that chronic bombesin treatment inhibited the growth of human ductal adenocarcinoma transplanted into athymic mice. These results were surprising for bombesin stimulates the growth of normal pancreatic tissue. The demonstration of both stimulatory and inhibitory activity of bombesin suggests that bombesin interacts differently in normal and neoplastic tissues.

These observations prompted us to evaluate the effect of BIM-26096 on the in vitro growth of a pancreatic tumor cell line (AR42J, ATCC No. CRL1492). For these experiments, AR42J cells were subcultured into a 24-well culture plate in Dulbecco's modified Eagle's medium containing 10% fetal calf serum and various concentrations (0.1–100 nM) of BIM-26096. After 36 hr. of incubation, the cells were removed with a trypsin/EDTA solution and the number of cells were determined using a Coulter counter. The results are as follows.

| Treatment control BIM-26096 | Cell Count (% Control) |
| --- | --- |
|  | 100 |
| (0.1 nM) | 78 |
| (1.0 nM) | 73 |
| (10 nM) | 56 |
| (100 nM) | 52 |

These results indicate that the bombesin agonist, BIM-26096, has in vitro antiproliferative activity against the AR42J rat pancreas tumor.

Bombesin and Bombesin analogs have been shown to inhibit the effect of interleukin-2 (IL-2) (Fink et al., 1988, Klin. Wochenschr. 66, Suppl. 13, 273). Since IL-2 causes T lymphocytes to proliferate, it is possible that Bombesin antagonists may prevent the inhibitory effect of Bombesin or its analogs on IL-2. IL-2 stimulated lymphocytes are capable of effectively lysing small cell lung carcinoma cells in vitro. Although Bombesin antagonists have a direct antiproliferative effect on neoplastic tissues, they may also favor proliferation of lymphocytes having lytic activity for small cell lung carcinoma.

Finally, Table 1 also shows that bond placement, while important, is not the only factor influencing antagonist activity, and that amino acid substitutions at some positions exert influence as well; this is illustrated by BIM-26030, with Gly in position 11, which exhibited no antagonist activity. Table 1 also gives negative results for analogs of Spantide ([D-Arg', D-Trp$^{7,9}$, Leu"] Substance P, and Bombesin. Thus the non-peptide bond placement guidelines given herein should be used in conjunction with the routine assays described above to select useful antagonists or agonists.

In a phase 5 assay, above, the results of which are not given in Table 1, BIM-26028 was shown to be a potent inhibitor of bombesin-stimulated gastric acid secretion.

Synthesis of Bradykinin Analogs

The synthesis of Boc-Arg(tosyl)Pro-Pro-Gly-Phe-$\psi$ [CH$_2$NH]-Ser(benzyl)-Pro-Phe-Arg(nitro)-O-resin is carried out as follows.

Boc-Arg(nitro)-polystyrene resin (Vega Biochemicals) (0.86 gm, 0.5 mmole) is placed in the reaction vessel of an Advanced ChemTech ACT 200 peptide synthesizer programmed to perform the following reaction cycle: (a) methylene chloride wash; (b) 33% trifluoroacetic acid in methylene chloride (2 times for 1 and 25 min each); (c) methylene chloride wash; (d) 10% triethylamine in dimethylformamide; (e) methylene chloride wash.

The neutralized resin is stirred with Boc-Phe and diisopropylcarbodiimide (1.5 mmole each) in methylene chloride for 1 h and the resulting amino acid resin is then cycled through steps (a) to (e) in the above wash program. The Boc group is then removed by TFA treatment and the following amino acid derivatives (1.5 mmole) are then coupled successively by the same procedure: Boc-Phe, Boc-Pro, Boc-Ser(benzyl). Boc-Phe aldehyde (1.5 mmoles), prepared by the method of Fehrentz and Castro (supra) is dissolved in 5 ml of dry DMF and added to the resin TFA salt suspension followed by the addition of 400 mg (8 mmoles) of sodium cyanoborohydride (Sasaki and Coy, supra, Coy et al., supra). After stirring for 1 h, the resin mixture is found to be negative to ninhydrin reaction (1 min) indicating complete derivatization of the free amino group.

After removal of the Boc group, Boc-Gly-p-nitrophenyl ester (3.0 mmoles) is then coupled in dimethylformamide. The following amino acids (1.5 mmole) are then coupled successively by the carbodiimide procedure: Boc-Pro, Boc-Pro, Boc-Arg(nitro). After drying, the peptide resin weighs 1.23 g.

The analog wherein the pseudopeptide bond is instead positioned between amino acids 8 and 9 (Phe and Arg) was made in analogous fashion.

The synthesis of H-Arg-Pro-Pro-Gly-Phe-$\psi$[CH$_2$NH]-Ser-Pro-Phe-Arg-OH follows.

The resin, as described above, (1.23 g, 0.5 mmole) is mixed with anisole (5 ml) and anhydrous hydrogenfluoride (35 ml) at 0° C. and stirred for 45 min. Excess fluoride is evaporated rapidly under a stream of dry nitrogen and free peptide precipitated and washed with ether. The crude peptide is dissolved in a minimum volume of 2M acetic acid and eluted on a column (2.5×95 cm) of Sephadex G-25. Fractions containing a major component by uv absorption (254 nm) and thin layer chromatography are then pooled, evaporated to a small volume and applied to a column (1.5×50 cm) of Vydac octadecylsilane (10–15 µM).

The peptide is eluted with a linear gradient of 10–35% acetonitrile in 0.1% trifluoroacetic acid in water. Fractions are examined by thin layer chromatography and analytical high performance liquid chromatography and pooled to give maximum purity. Repeated lyophilization of the solution from water gives 104 mg of the product as a white, fluffy powder.

The product is found to be homogeneous by hplc and tlc. Amino acid analysis of an acid hydrolysate confirms the composition of the octapeptide. The presence of the Pheψ[CH$_2$NH] peptide bond is also demonstrated by fast atom bombardment mass spectrometry.

Other peptides can be prepared in similar yields in an analogous fashion by appropriately modifying the above procedure.

A linear bradykinin analog can be tested for effectiveness as either an agonist or antagonist of bradykinin using the following method.

Cell Culture

Described below is an assay method that employs cultured neuroblastoma cells, which have high-affinity receptor sites for bradykinin and respond to bradykinin with an increase in intracellular levels of cyclic GMP. Mouse neuroblastoma cells (Clone N1E-115) were obtained from Dr. Elliott Richelson (Mayo Clinic and Foundation, Rochester, Minn., Snider and Richelson, 1984, J. Neurochem. 43:1749–1754) and cultured in Dulbecco's modified Eagle's medium (Sigma Chem., St. Louis, Mo.) without antibiotics and supplemented with 10% fetal calf serum (Sigma Chem.). The stock cultures were grown in an atmosphere of 10% CO$_2$/90% humidified air.

Bradykinin-Stimulated cyclic GMP Formation

The assay of cyclic GMP formation was modified from the procedure described by Snider and Richelson (1984). The cells were initially grown for five days in 24-well culture plates. On the day of assay the culture medium was then removed, and the cells were washed twice with a phosphate-buffered saline solution (PBS) containing 110 mM NaCl, 5.3 mM KCl, 1.8 mM CaCl$_2$, 1.0 nM MgCl$_2$, 2.0 mM Na$_2$HPO$^4$, 25 mM glucose, and 70 mM sucrose (pH 7.4, 335–340 mmol). The cells were labeled with [$^3$H]guanine (4 μCi/ml, 0.6 μM) in PBS for 45 min at 37° C. After the [$^3$H]guanine incubation he PBS/[$^3$H]guanine solution was removed and each well was washed an additional time with PBS. PBS (240 μl) and antagonists (30 μl) were added, and the cells were pre-incubated for 10 min (37° C.). To assay for agonist activity, either Bradykinin or the test compound (30 μl) (Bachem Inc., Torrence, Calif.) was added, and the incubation was continued for an additional 30 sec. (37 C.). To test for antagonist activity, labeled cells were pre-incubated for 5 min. with the test antagonist before the addition of Bradykinin (indicated as "+" in results of antagonist assays, below). The Bradykinin or test compound stimulation was terminated by the addition of 30 μl of 50% (w/v) trichloroacetic acid, and the contents of each well were transferred to (0.8×8.0 cm) AG50 W-X2 ion exchange column which had been equilibrated with 0.1N HCl. The columns were then sequentially washed with 4.4 ml of 0.1N HCl (eluate discarded), 1.0 ml H$_2$O (eluate discarded), and 1.5 ml H$_2$O which was collected into 12×75 mm plastic culture tubes. To this last eluate, equal volumes (30 μl) of 2.67M ZnSO$_4$ and 2.67M Na$_2$CO$_3$ were added to further precipitate any residual [$^3$H]GDP or [$^3$H]GTP. After the precipitate had been removed by centrifugation, the supernatant was transferred to 7 ml of Scint A (Packard) and the radioactivity determined by liquid scintillation spectrometry.

[$^3$H]Bradykinin Binding Experiments

Membranes from the cells were prepared by homogenizing the N1E-115 cells in ice-cold buffer with a Brinkman Polytron (seting 6, 15 sec) and centrifuging twice (39,000 g. 10 min.) with an intermediate resuspension in fresh buffer. Aliquots of the membrane preparation were incubated with 1.0 nM (competition experiments) or 0.3–5 nM (saturation experiments) [$^3$H]bradykinin (88.7 Ci/mmol, New England Nuclear) for 90 min (25° C.) in a final volume of 1.0 ml. The binding assay was terminated by rapid filtration through Whatman GF/B filters that had previously soaked in 0.1% aqueous polyethyleneimine. Each assay tube and filter were immediately washed three times with 5 ml aliquots of ice-cold buffer, and the bound radioactivity trapped on the filters were counted by liquid scintillation spectrometry.

As shown in Table III, incubation of N$_1$E-115 cells with bradykinin produced a dose-dependent stimulation of cyclic GMP formation. Maximum stimulation of cyclic GMP formation (to ~6 pmoles) occurred at approximately 100 nM of bradykinin.

Results of Assays of Test Peptides

A true antagonist molecule binds to a specific receptor (i.e. the Bradykinin receptor) with the same affinity as an agonist but lacks biological activity.

An example of a true antagonist is BIM-31006, as shown below.

Assay for antagonist activity of BIM-31006

| Condition | cGMP response (dpm) |
| --- | --- |
| basal | 327 |
| bradykinin (3 nM) | 2459 |
| +BIM-31006 (1 nM) | 2004 |
| +BIM-31006 (10 nM) | 1201 |
| +BIM-31006 (100 nM) | 418 |

Assay for agonist activity of BIM-31006

| Condition | cGMP response (dpm) |
| --- | --- |
| basal | 437 |
| BIM-31006 (0.3 nM) | 424 |
| BIM-31006 (1.0 nM) | 335 |
| BIM-31006 (3.0 nM) | 448 |
| BIM-31006 (10 nM) | 266 |
| BIM-31006 (30 nM) | 333 |
| BIM-31006 (100 nM) | 427 |
| bradykinin (3 nM) | 3019 |

The results show that BIM-31006 does have antagonist activity in the concentration range of 1–100 nM, and does not have agonist activity in the same concentration range.

A molecule may appear to be an antagonist, but not be a true antagonist, if it acts as a superagonist by causing over-stimulation of its target receptor and thus desensitizes the receptor to stimulation. This is a mechanism by which a molecule that is a superagonist may appear to be an antagonist. An example of this type of pseudo-antagonist is D-Arg$^0$, Hyp$^3$, Phe$^8$ψ[CH$_2$NH]BK, or BIM-31012.

BIM-31012 is an example of an antagonist which acts by desensitization of the receptor. The antagonist and agonist activities was shown in the following experiment:

Assay for antagonist activity of BIM-31012

| Condition | cGMP response (dpm) |
| --- | --- |
| basal | 279 |
| bradykinin (3 nM) | 1929 |

| Condition | cGMP response (dpm) |
|---|---|
| +BIM-31012 (0.1 nM) | 1818 |
| +BIM-31012 (1 nM) | 516 |
| +BIM-31012 (10 nM) | 401 |
| +BIM-31012 (100 nM) | 296 |

Therefore, in concentrations between 1–100 nM, BIM-31012 is an antagonist.

Assay for agonist activity of BIM-31012

| Condition | cGMP response (dpm) |
|---|---|
| basal | 279 |
| BIM-31012 (1 nM) | 1379 |
| BIM-31012 (10 nM) | 4608 |
| BIM-31012 (100 nM) | 5938 |

These results show that, in the same concentration range, BIM-31012 is also an agonist. To determine if the apparent antagonistic activity of BIM-31012, shown above, was a result of agonist-induced receptor desensitization, the cells were preincubated with bradykinin for 5 min. at 37° C. before assaying for Bradykinin-stimulated cGMP formation.

| Condition | cGMP response (dpm) |
|---|---|
| basal | 385 |
| bradykinin (3 nM) | 2085 |
| +bradykinin (1 nM) | 1655 |
| +bradykinin (10 nM) | 1591 |
| +bradykinin (100 nM) | 496 |
| +bradykinin (1000 nM) | 348 |

The results demonstrate that pre-incubation of cells with bradykinin results in apparent antagonistic activity for bradykinin itself, which is normally an agonist. This suggests that the initial exposure to bradykinin over-stimulated the receptor and thus desensitized it, which also explains the apparent antagonism of BIM-31012.

Other bradykinin analogs may be mixed antagonist/agonists; i.e., may be true antagonists over a given concentration range, but agonists at a different concentration range. BIM-31005 may also be a mixed antagonist/agonist, as shown by the following experiments.

Assay for agonist activity of BIM-31005

| Condition | cyclic GMP response (dpm) |
|---|---|
| basal | 265 |
| BIM-31005 (0.1 nM) | 246 |
| BIM-31005 (0.3 nM) | 260 |
| BIM-31005 (1.0 nM) | 306 |
| BIM-31005 (3.0 nM) | 227 |
| BIM-31005 (10 nM) | 1481 |
| BIM-31005 (30 nM) | 3705 |
| Bradykinin (3.0 nM) | 3821 |

The results show that BIM-31005 is less potent than Bradykinin as an agonist. BIM-31005, however, binds with higher affinity to the receptor than Bradykinin. The Ki for BIM-31005 is 0.38 nM, and for bradykinin is 1.0 nM. Table III and the assay below show antagonist activity of BIM-31005.

| Condition | cyclic SMP response (dpm) |
|---|---|
| basal | 327 |
| bradykinin (3.0 nm) | 2594 |
| +BIM-31005 (1.0 nM) | 2459 |
| +BIM-31005 (10 nM) | 1390 |
| +BIM-31005 (100 nM) | 538 |

These results suggest that the antagonistic activity of BIM-31005 begins to occur at 1.0 nM; at this concentration, no agonist activity is observed. This suggests a mixture of agonist/antagonist activities. BIM-31005 may also act antagonistically by desensitizing the receptor at those concentrations at which it appears to act as an antagonist.

Another example of a mixed antagonist/agonist is D-Arg$^0$, Hyp$^3$, Phe$^5\psi$[CH$_2$NH]BK, or BIM-31011. The experimental results for this analog are shown below:

Assay for antagonist activity of BIM-31011

| Condition | cGMP response (dpm) | % inhibition |
|---|---|---|
| basal | 308 | — |
| Bradykinin (3 nm) | 6968 | — |
| +BIM-31011 | | |
| (1 nm) | 4757 | 33 |
| (10 nm) | 4619 | 35 |
| (100 nm) | 2886 | 61 |
| (1000 nm) | 320 | 99 |

Assay for agonist activity of BIM-31011

| Condition | cGMP response (dpm) |
|---|---|
| basal | 308 |
| BIM-31011 | |
| (0.1 nm) | 238 |
| (1.0 nm) | 325 |
| (10 nm) | 314 |

This compound shows antagonist activity in the range of 1–1000 nM and no agonist activity up to 10 nM.

The sharp drop in antagonist activity seen above between 100 nM and 1000 nM was investigated further.

Assay for antagonist activity of BIM-31011

| Condition | cGMP response (dpm) | % inhibition |
|---|---|---|
| basal | 102 | — |
| bradykinin (3 nM) | 1882 | — |
| +BIM-31011 (100 nM) | 1632 | 14 |
| +BIM-31011 (300 nM) | 852 | 58 |
| +BIM-31011 (1000 nM) | 166 | 96 |

Assay for agonist activity of BIM-31011

| Condition | cGMP response (dpm) |
|---|---|
| basal | 179 |
| BIM-31011 (100 nM) | 146 |
| BIM-31011 (300 nM) | 281 |
| BIM-31011 (1000 nM) | 1987 |
| bradykinin (3 nM) | 1336 |

The results show that antagonist activity of BIM-31011 starts to decrease at a concentration of 300 nM and completely disappears at 1000 nM, whereas agonist activity is markedly stimulated at 1000 nM. BIM-31011 is therefore a mixed agonist/antagonist. The Phe[5]- and Phe[8]-ψ[CH$_2$NH]-bradykinin antagonists are as potent as other analogues, such as those developed by Stewart (Schachter et al., 1987, Br. J. Pharmac. 92:851–855; Rifo et al., 1987, Eur. J. Pharmac. 142:305–312; Vavrek and Stewart, 1985, Peptides 6:161–164; Steranka et al., 1987, Eur. J. Pharmac. 136:261–262).

LHRH Antagonists

As is described below, there were synthesized eight non-peptide bond-containing analogs of luteinising hormone-releasing hormone (LHRH), which in its natural state has the structure

p-Glu-His-Trp-Ser-Tyr-Gly-Leu-Arg-Pro-Gly-NH$_2$;

antagonists of LHRH are of medical use as agents for the therapeutic control of fertility and hormone dependent tumors. The non-peptide bond-containing antagonists are listed (numbers III-X) in Table 2; they are all analogs of the LHRH antagonist [N-Ac-D-Nal[1], D-Phe[2,3], D-Arg[6], Phe[7], D-Ala[10]] LHRH.

Synthesis of Non-Peptide Bond-Containing Analogs

The first step was the preparation of protected amino acid aldehydes, which was carried out by the method of Fehrentz and Castro (Synthesis (1983) 676) as follows. The protected amino acids were convered to the corresponding N,O-dimethylhydroxamates by reaction with an excess of N,O-dimethylhydroxylamine hydrochloride (1.5 equiv) and dicyclohexylcarbodiimide (1.5 equiv) in dichloromethane containing an excess of diisopropylethylamine (4 equiv) at 0° C. The reaction was allowed to warm up to ambient temperature over 16 h with stirring. The crude N,O-dimethylhydroxamates were isolated as oils after washing with 3M HCl (3×30 mL), saturated NaHCO$_3$ solution (3×30 mL), water (3×30 mL), drying over MgSO$_4$ and evaporation to dryness at reduced pressure. The N,O-hydroxamates were then reduced with LiAlH$_4$ in ether/-tetrahydrofuran at 0° C. The reaction followed by TLC, and worked up as above to give the crude protected amino acid aldehydes.

The peptides were assembled on 4-methylbenzhydrylamine functionalized (ca. 0.7 mequiv g$^{-1}$) 1% crosslinked polystyrene resin, on 1 mmol scales utilising a Vega Model 50 synthesiser, using a modified solid phase procedure. The reduced peptide bonds were formed by the reductive alkylation of the deprotected N$_\alpha$-amino group with the appropriate protected amino acid aldehyde (3.0 equiv.) in the presence of NaBH$_3$CN (10 equiv.) in DMF (25 mL) containing 1% acetic acid at ambient temperature for 16 h.

The decapeptides were cleaved from the resin support, with simultaneous side-chain deprotection, by acidolysis using anhydrous hydrogen fluoride containing anisole (~0.3% w/v) as scavengers for 1 h at 0° C.

To effect purification, the crude peptides were subjected initially to gel permeation chromatography on Sephadex G25(2.5×100 cm) with 50% acetic acid eluent to achieve desalting. Final purification was effected by preparative RP-HPLC on C$_{18}$ bonded silica gel (Vydac C$_{18}$, 10–15 µm, 0.10×45 cm) eluted with a linear acetonitrile gradient with a constant concentration of trifluoroacetic acid (0.1% v/v). The linear gradient was generated using a Chromat-a-Trol Model II (Eldex Laboratories, Inc.) gradient maker. The separations were monitored at 280 nm, by TLC on silica gel plates (Merck F60) and by analytical RP-HPLC. The fractions containing the product were pooled, concentrated in vacuo, and subjected to filtration. Each peptide was obtained as a fluffy white powder of constant weight by lyophilization from aqueous acetic acid. The purity of the final peptides was assessed by RP-HPLC and TLC in five solvent systems.

LH-RH Antiovulatory and Antihistamine Activities

The antiovulatory activity of each analogue was determined in Sprague Dawley rats in a standard assay (Vilchez-Martinez et al. (1976) Endocrine Res. Comm. 3:231) using a 40% propan-1-2diol/0.9% saline vehicle. The results (given in Table 2) are expressed as the percentage of (n) rats which did not ovulate at a dose of x micrograms of analogue. The in vitro histamine releasing activity of each analogue was determined using peritoneal mast cells from male Sprague-Dawley rats in a standard assay (Karten et al. in LH-RH and its Analogs Contraceptive and Therapautic Applications: Part II, eds. Vickery et al. MTP Press Ldt., Hingham Ma 1987.) (Standard Compound 48/80 has an ED$^{50}$=0.58 in this assay system).

Although the reduced peptide bond analogs all had lower antiovulatory activities than the parent antagonist (see Table 2), with many having no measurable activity at the 50 µg dose (peptides III, IV, V and IX), the modifications had little significant effect on the in vitro histamine releasing activities of the peptides. Several analogues still maintained significant antiovulatory activity.

Mechanism of Antagonism

According to the calculated structure of LH-RH, the β-bend is stabilised by transannular hydrogen bonds between Tyr[5] and Arg[8]. Peptide VII, which has no Tyr[5] (CO), would be unable to form one of these hydrogen bonds, yet it is the most active of this series of analogues (VII, 100% at 12 µg,ED$_{50}$=1.50). The N-terminus is held in close proximity to the C-terminus and it is possible that hyrdogen bonding occurs between Ac(CO) and D-Ala[10](NH$_2$). The antiovulatory activity of peptide I (N-ethyl-D-Nal[1],17% at 6 µg,ED$_{50}$=0.34) is much lower than the parent peptide (56% AOA at 0.5 µg), which is in accordance with either the loss of an N to C terminal hydrogen bond, or the loss of a crucial interaction of the acetyl carbonyl with the receptor. Likewise, the loss of a putative transannular hydrogen bond between D-Phe[3](CO) . . . D-Ala[10](NH) seems to correspond to the loss of activity with peptide V. Peptide X (Pro[9]-ψ[CH$_2$NH]D-Ala[10],44% at 6 µg,ED$_{50}$=0.21), peptide VI(Ser[4]ψ[CH$_2$NH]Tyr[5],63% at 12 µg,ED$_{50}$=0.43), and peptide VIII(D-Lys[6]ψ[CH$_2$NH]Phe[7], 60% at 50 µg,ED$_{50}$=1.90) maintained significant activity, a finding which is consistent, as none are involved in possible transannular hydrogen bonding. Indeed, each modification is situated between residues which are involved in internal hydrogen bonding, and therefore the flexibility conferred by the reduced peptide bond is constrained. Replacements in the pendant, hydrophobic N-terminus presumably introduce excessive flexibility and loss of activity.

Use

The peptides of the invention may be administered to a mammal, particularly a human, in one of the traditional modes (e.g., orally, parenterally, transdermally, or transmucosally), in a sustained release formulation using a biodegradable biocompatible polymer, or by on-site delivery (e.g., in the case of anti-cancer bombesin to the lungs) using micelles, gels and liposomes.

The bombesin antagonists and agonists of the invention are suitable for the treatment of all forms of cancer where bombesin-related substances act as autocrine or paracrine mitotic agents, particularly small-cell lung carcinoma. The peptides can also be used for the inhibition of gastric acid secretion, the symptomatic relief and/or treatment of exocrine pancreatic adenocarcinoma, and the restoration of appetite to cachexic patients. The peptides can be administered to a human patient in a dosage of 0.5 μg/kg/day to 5 mg/kg/day. For some forms of cancer, e.g., small cell lung carcinoma, the preferred dosage for curative treatment is 250 mg/patient/day.

The bradykinin peptides of the invention are antagonists/agonists in the neuroblastoma system described herein. Bradykinin antagonists and agonists of the invention are suitable for the treatment of vascular tone disorders, e.g., vascular permeability-induced pain (common cold symptoms, edema caused by brain trauma, hemorrhage-induced shock, or poison ivy) can be treated with antagonists, as can pain and arthritis. Agonists can be used to relieve hypertension or to facilitate repair of damaged tissue. The peptides can be administered (most preferably, topically) to a human patient in a dosage of 0.5 μg/kg day to 5 mg/kg/day, preferably 10–1000 μg/kg/day.

Other Embodiments

Other embodiments are within the following claims.

For example, as is mentioned above, there are a number of other peptide families from which agonists or antagonists can be made according to the invention. Some of these families are substance P and related peptides, vasoactive inestial peptide (VIP) and related peptides, and neurotensin and related peptides. The number of peptides in each family on which antagonists or agonists can be based is large. For example, there are at least 10 currently-known peptides in the VIP family, including sauvagine and urotensin. In addition, there have been isolated seven natural bradykinin-like peptides. Neurotensin (pGlu-Leu-Tyr-Glu-Asn-Lys-Pro-Arg-Arg-Pro-Tyr-Ile-Leu-OH) has two peptide bonds which advantageously can be replaced by non-peptide bonds: Ile-Leu and Tyr-Ile. In addition, neurotensin antagonists can be missing any or all of the N-terminal seven amino acid residues, as it has been shown (Granier et al. (1984) Eur. J. Biochem. 124: 117) that they are not needed for biological activity and binding. Screening of neurotensin antagonists can be by binding to SCLC receptors. Gastrin releasing peptides (GRP) and related peptides (e.g., Neuromedin C (GRP 18–27)) have a bond between amino acid residues 13 and 14 which can be replaced with a non-peptide bond to form a GRP antagonist. Other peptides for which antagonists can be made according to the invention are ACTH and related peptides, and angiotensin and related peptides. In addition, LHRH and LHRH agonists can be made into antagonists according to the invention. The same may also apply to lymphokines such as interleukins and to growth factors such as EGF, IGF, and their biologically active fragments.

TABLE 1

| Code | Structure | Brain GRP Receptor IC50 (nM) | 3T3 GRP Receptor IC50 (nM) | Thym. Uptake IC50 (nM) |
|---|---|---|---|---|
| BIM-26025 | [His$^{12}$Ψ[CH$_2$NH]Leu$^{14}$]BN | >1000 | | |
| BIM-26026 | [Ala$^9$Ψ[CH$_2$NH]Leu$^{14}$]BN | >1000 | | 1574 |
| BIM-26027 | [Val$^{10}$Ψ[CH$_2$NH]Leu$^{14}$]BN | 0.48 | 2.3 | agonsit EC50 = 0.07 nM |
| BIM-26028 | [Leu$^{13}$Ψ[CH$_2$NH]Leu$^{14}$]BN | 13 | 16 | 14.7 |
| BIM-26030 | [Gly$^{11}$Ψ[CH$_2$NH]Leu$^{14}$]BN | >1000 | | |
| BIM-26034 | [Gln$^7$Ψ[CH$_2$NH]]BN | >1000 | | |
| BIM-26036 | [Des-pGlu$^1$, Gln$^2$, ala$^9$ Ψ[CH$_2$NH]Phe$^{12}$]BN | >1000 | | |
| BIM-26046 | [Gly$^{11}$Ψ[CH$_2$NH]D—Phe$^{12}$ Leu$^{14}$]BN | >1000 | | |
| BIM-26048 | [D—Phe$^{12}$Ψ[Ch$_2$NH]Leu$^{13}$ Leu$^{14}$]BN | >1000 | | |
| BIM-26056 | [Leu$^{10}$Ψ[CH$_2$NH] Leu$^{11}$NH$_2$]Substance P | >1000 | | |
| BIM-26057 | [Cys$^9$, ΨLeu$^{13}$, Cys$^{14}$]BN | >1000 | | |
| BIM-26061 | [D-pGlu$^1$, d—Ala$^5$, Leu$^7$ Ψ[CH$_2$NH]Met$^8$]BN | >1000 | | |
| BIM-26062 | [Phe$^{13}$Ψ[CH$_2$NH] Leu$^{14}$]BN | >1000 | | 437 |
| BIM-26063 | [des-Gln$^7$, Leu$^{13}$ Ψ[CH$_2$NH]Leu$^{14}$]BN | >1000 | | |
| BIM-26064 | [ΨLeu$^{10}$, Nle$^{11}$]Spantide | >1000 | | |
| BIM-26067 | [des-Gln$^7$, Leu$^{13}$ Ψ[CH$_2$NH]BN | 1000 | | |
| BIM-26068 | [Leu$^{13}$Ψ[CH$_2$NH]Phe$^{14}$]BN | 2.9 | | 70 |
| BIM-26070 | [D—Trp$^9$Ψ[CH$_2$Nh], Nle$^{11}$] Spantide | >1000 | | |
| BIM-26071 | [Tyr$^4$, Leu$^{13}$Ψ[CH$_2$NH]- Met$^{14}$]BN | 34 | 16 | 104 |
| BIM-26072 | [Cys$^9$, Leu$^{13}$Ψ [CH$_2$NH]Cys$^{14}$]BN | 1000 | | |
| BIM-26074 | [Des-Gln$^7$, Leu$^{13}$Ψ | 1000 | | |

TABLE 1-continued

| Code | Structure | Brain GRP Receptor IC50 (nM) | 3T3 GRP Receptor IC50 (nM) | Thym. Uptake IC50 (nM) |
|---|---|---|---|---|
| BIM-26075 | [D—Phe$^{11}$, Leu$^{13}$Ψ [CH$_2$Nh[Leu$^{14}$]BN [CH$_2$NH]Leu$^{14}$]BN | >1000 | | |
| BIM-26076 | [D—Phe$^{11}$, Leu$^{13}$Ψ[CH$_2$NH] Leu$^{14}$]BN | >1000 | | |
| BIM-26077 | [D—Ala$^5$, Leu$^{13}$Ψ[CH$_2$NH] Leu$^{14}$]BN | 517 | 196 | 1001 |
| BIM-26078 | [D—Ala$^{11}$, Leu$^{13}$Ψ[CH$_2$NH] Leu$^{14}$]BN | >1000 | | 70 |
| BIM-26079 | [Phe$^7$Ψ[CH$_2$NH], Leu$^{11}$] Spantide | >1000 | | |
| BIM-26080 | [Gln$^6$Ψ[CH$_2$NH], Nle$^{11}$] Spantide | >1000 | | |
| BIM-26081 | [D—Trp$^7$Ψ[CH$_2$NH]-Nle$^{11}$] Spantide | >1000 | | |
| BIM-26082 | [Phe$^8$Ψ[CH$_2$NH]-Nle$^{11}$] Spantide | >1000 | | |
| BIM-26083 | [Gln$^6$Ψ[CG$_2$NH]-Nle$^{11}$] Spantide | >1000 | | |
| BIM-26084 | [D—Trp$^7$Ψ[CH$_2$NH]-Nle$^{11}$] Spantide | >1000 | | |
| BIM-26085 | [Phu$^8$Ψ[CH$_2$NH]-Nle$^{11}$] Spantide | >1000 | | |
| BIM-26086 | [D—Phe$^{12}$, LeuΨ[CH$_2$Nh] Leu$^{14}$]BN | >1000 | | |
| BIM-26088 | [Gly$^9$Ψ[CH$_2$NH]Leu$^{14}$] Spantide | >1000 | | |
| BIM-26089 | [Gln$^6$Ψ[CH$_2$NH]Leu$^{11}$] Spantide | >1000 | | |
| BIM-26090 | [Phe$^7$Ψ[CH$_2$NH]Leu$^{11}$] Substance P | | | >1000 |
| BIM-26091 | [Phe$^8$Ψ[CH$_2$NH]Leu$^{11}$] Substance P | | | >1000 |
| BIM-26092 | [Leu$^9$Ψ[CH$_2$NH]Neuromedin C | | 242 | 466 |
| BIM-26093 | des$^{1-4}$, D—Ala$^5$, His$^7$, Leu$^{13}$ Ψ[CH$_2$NH]BN | | 82 | 171 |
| BIM-26094 | [D—Ala$^{5,11}$, Leu$^{13}$Ψ[CH$_2$NH] Leu$^{14}$]BN | | 1613 | 574 |
| BIM-26095 | [D—Ala$^6$, Leu$^9$Ψ[CH$_2$NH] Leu$^{10}$]Litorin | | 2623 | 1209 |
| BIM-26096 | [Sta$^{13}$, Des Met$^{14}$]BN | | 33 | agonsit EC50 = 3 nM |
| BIM-26097 | [Ac—Lys$^7$, Leu$^{13}$Ψ[CH$_2$NH]]BN | 1000 | | >1000 |
| BIM-26098 | [Lys$^7$, Leu$^{13}$Ψ[CH$_2$NH]]BN | 1000 | | |
| BIM-26099 | [Leu$^{13}$Ψ[CH$_2$NH], Met]BN | | 76 | 78 |
| BIM-26100 | [Phe$^8$Ψ[CH$_2$NH]Leu$^9$]Litorin | | 74 | 22 |
| BIM-26101 | Leu$^8$Ψ[CH$_2$NH]Leu$^9$]Litorin | | 17.9 | 257 |
| BIM-26102 | des$^{1-4}$, Leu$^7$, thr$^{10}$, Phe$^{13}$ Ψ[CH$_2$NH]BN | | 184 | >1000 |
| BIM-26103 | Leu$^{13}$Ψ[CH$_2$NH]Met$^{14}$NH2 A-Lytensin | >1000 | | >1000 |
| BIM-26104 | des$^{1-6}$, His$^7$, Leu$^{13}$ Ψ[CH$_2$NH]BN | | | >1000 |
| BIM-26105 | D—Ala$^{1,7}$, Leu$^9$Ψ[CH$_2$CH] Neuromedin C | | | 107 |
| BIM-26106 | desGly$^1$, D—Ala$^{2,7}$, Leu$^9$ 105 [CH$_2$NH]Neuromedin C | | | 10.0 |
| BIM-26107 | D—Phe$^1$, Leu$^9$Ψ[CH$_2$NH] Neuromedin C | | | 154 |
| BIM-26108 | N—Ac—D—ala$^1$, Leu$^9$Ψ [CH$_2$NH]Neuromedin C | | | >1000 |
| Spantide | [D—Arg$^1$, D—Try$^{7,9}$, Leu$^{11}$] Substance P | | 3303 | 2171 |
| Bombesin | pGlu—Gln—Arg—Leu—Gly—Asn—Gin—Trp—Ala—Ala—Gly—His—Leu—Met—NH$_2$ | 1.5 | 0.17 | |

TABLE 2

Antiovulatory and Histamine Releasing Activities of Analogues with the General Formula [N—Ac—D—Nal¹, D—Phe²,³, D—Arg⁶, Phe⁷, D—Ala¹⁰] LH.RH Containing the Ψ[CH₂NH] Isostere

| Peptide | Reduced peptide bond | Antiovulatory activity* | in vitro Histamine release $ED_{50}^{b}$ |
|---|---|---|---|
|  | Parent analogue | 56 at 0.5 (9) | 0.11 ± 0.04 |
| I | N-ethyl-D—Dal¹ | 17 at 6 (6) | 0.34 ± 0.10 |
|  |  | 82 at 12 (11) |  |
| II | N,N-diethyl-D—Nal¹ | at 6 (9) | 0.45 ± 0.04 |
| III | D—Nal¹ Ψ[CH₂NH] D—Phe² | at 50 (9) | 1.50 ± 0.33 |
| IV | D—Phe² Ψ[CH₂NH] D—Phe³ | 0 at 50 (7) | 0.35 ± 0.09 |
| V | D—Phe³ Ψ[CH₂NH] Ser⁴ | at 50 (11) | 0.43ᶜ |
| VI | Ser⁴ Ψ[CH₂NH] tyr⁵ | 63 at 12 (8) | 0.19ᶜ |
| VII | Tyr⁵ Ψ[CH₂NH] D—Arg⁶ | 100 at 12 (8) | 1.50 ± 0.29 |
| VIII | D—Lys⁵ Ψ[CH₂NH] Phe⁷ | 60 at 60 (10) | 1.90 ± 0.06 |
| IX | Phe⁷ Ψ[CH₂NH] Arg⁸ | 0 at 50 (11) | 0.46 ± 0.03 |
| X | Pro⁹ Ψ[CH₂NH] D—Ala¹⁰ | 44 at 6 (9) | 0.21ᶜ |
|  |  | 92 at 12 (13) |  |

*Expressed as the percentage of (n) rats blocked at a dose of X ug.
ᵇExpressed as the mean $ED_{50}$ = standard error in units of ug ml⁻¹.
ᶜMean of 2 determinations.

TABLE III

Bradykinin Antagonists - Receptor Binding and Biological Activity

| Compound | Structure | Receptor Binding Ki (nM)* | cyclic GMP Antagonism Ki (nM)** |
|---|---|---|---|
| BIM-31002 | Phe⁵Ψ[CH₂NH]BK | 1.0 ± 0.36 | 8.4 ± 3.8 |
| BIM-31003 | G;y4Ψ[CH₂NH]BK | 2215 ± 298 | >10000 |
| BIM-31004 | Pro⁷Ψ[CH₂NH]BK | 11 ± 1.3 | 97 ± 56 |
| BIM-31005 | Phe⁸Ψ[CH₂NH]BK | 0.38 ± 0.07 | 9.1 ± 2.1 |
| BIM-31006 | [D—Arg⁰, Hyp³, D—Phe⁷]BK | 0.24 ± 0.05 | 14 ± 1.7 |
| BIM-31007 | Pro³Ψ[C₂NH]BK | 48 ± 8.6 | >10000 |
| BIM-31008 | Lys¹,⁹, Phe⁸Ψ[CH₂NH]BK | 2294 | >10000 |
| BIM-31009 | Phe⁵,⁸Ψ[CH₂NH]BK | >10000 | >10000 |

*Inhibition of 1.0 nM[³H]bradykinin binding to mouse neuroblastoma cells (clone N1E-115)
**Inhibition of bradykinin (30 nM) - stimulated cyclic GMP formation in mouse neuroblastoma cells (clone N1E-115).

We claim:

1. A bradykinin antagonist of the following amino acid formula:

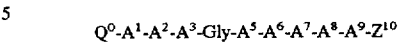

wherein $Q^0$ is H;

$A^1$ is L-Arg, D-Arg, L-homo-Arg, or D-homo-Arg;

$A^2$ is Pro, or Hyp;

$A^3$ is Pro, or Hyp;

$A^5$ is Phe, or thienylalanine;

$A^6$ is Ser, or Thr;

$A^7$ is Pro, or Hyp;

$A^8$ is Phe, p-X-Phe in which X is F, Cl, Br, OH, or $CH_3$, or thienylalanine;

$A^9$ is Arg, or homo-Arg;

$Z^{10}$ is OH; and for each of the residues $A^5$, $A^6$, $A^7$, and $A^8$, independently, the carbon atom participating in the amide bond between that residue and the nitrogen atom of the α-amino group of the adjacent amino acid residue is either a carbonyl carbon or is reduced to a methylene carbon, provided that at least one such carbon atom must be reduced to a methylene carbon; or a pharmaceutically acceptable salt thereof.

2. A peptide of claim 1, wherein the carbon atom participating in the amide between $A^5$ and the nitrogen atom of the α-amino group of the adjacent amino acid residue is reduced to a methylene carbon.

3. A peptide of claim 1, wherein the carbon atom participating in the amide between $A^8$ and the nitrogen atom of the α-amino group of the adjacent amino acid residue is reduced to a methylene carbon.

* * * * *